(12) United States Patent
Nottmeier

(10) Patent No.: US 9,615,733 B2
(45) Date of Patent: Apr. 11, 2017

(54) ANTERIOR CERVICAL RETRACTOR SYSTEM

(75) Inventor: Eric W. Nottmeier, Atlantic Beach, FL (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 512 days.

(21) Appl. No.: 13/445,571

(22) Filed: Apr. 12, 2012

(65) Prior Publication Data

US 2012/0265021 A1 Oct. 18, 2012

Related U.S. Application Data

(60) Provisional application No. 61/474,805, filed on Apr. 13, 2011.

(51) Int. Cl.
| | |
|---|---|
| A61B 1/32 | (2006.01) |
| A61B 1/313 | (2006.01) |
| A61B 17/70 | (2006.01) |
| A61B 17/02 | (2006.01) |
| A61B 90/50 | (2016.01) |
| A61B 17/17 | (2006.01) |
| A61B 90/57 | (2016.01) |

(52) U.S. Cl.
CPC .............. *A61B 1/32* (2013.01); *A61B 1/3135* (2013.01); *A61B 17/0206* (2013.01); *A61B 17/7059* (2013.01); *A61B 90/50* (2016.02); *A61B 17/1728* (2013.01); *A61B 17/1757* (2013.01); *A61B 2090/571* (2016.02)

(58) Field of Classification Search
USPC .................................................. 600/201–246
See application file for complete search history.

(56) References Cited

U.S. PATENT DOCUMENTS

| | | | |
|---|---|---|---|
| 3,572,326 A * | 3/1971 | Jensen ......................... 600/233 |
| 4,099,521 A * | 7/1978 | Nestor et al. ................. 600/228 |
| 4,457,300 A * | 7/1984 | Budde .......................... 600/228 |
| 5,512,038 A * | 4/1996 | O'Neal et al. ................ 600/210 |
| 5,795,291 A * | 8/1998 | Koros et al. .................. 600/232 |
| 6,099,468 A * | 8/2000 | Santilli et al. ................ 600/232 |
| 6,102,854 A * | 8/2000 | Cartier et al. ................ 600/228 |
| 6,206,826 B1 * | 3/2001 | Mathews et al. ............. 600/210 |
| 6,464,634 B1 * | 10/2002 | Fraser ........................... 600/233 |
| 7,736,380 B2 * | 6/2010 | Johnston et al. ............. 606/280 |
| 7,909,848 B2 * | 3/2011 | Patel et al. ................... 606/201 |

(Continued)

*Primary Examiner* — Mary Hoffman
(74) *Attorney, Agent, or Firm* — Quarles & Brady LLP

(57) ABSTRACT

An orthopedic surgery system includes: a retractor support arm; a table mounting assembly for securing the retractor support arm to the operating table; a first blade mounting arm slidably engaging the retractor support arm; a second blade mounting arm slidably engaging the retractor support arm in spaced relationship with respect to the first blade mounting arm; a first retractor blade connected to the first blade mounting arm; a second retractor blade connected to the second blade mounting arm; and a plate support assembly for releasably engaging an orthopedic plate wherein the plate support assembly slidably engages at least one of the retractor support arm or the first blade mounting arm or the second blade mounting arm. In one version of the invention, the system used in anterior cervical spine surgery and the orthopedic plate is an anterior cervical plate.

18 Claims, 5 Drawing Sheets

(56) References Cited

U.S. PATENT DOCUMENTS

| | | | |
|---|---|---|---|
| 8,100,828 B2* | 1/2012 | Frey et al. | 600/234 |
| 8,394,107 B2* | 3/2013 | Fanger et al. | 606/96 |
| 2004/0210232 A1* | 10/2004 | Patel et al. | 606/96 |
| 2005/0119531 A1* | 6/2005 | Sharratt | 600/227 |
| 2006/0084844 A1* | 4/2006 | Nehls | 600/227 |
| 2006/0206009 A1* | 9/2006 | Von Wald et al. | 600/231 |
| 2007/0179345 A1* | 8/2007 | Santilli | 600/227 |
| 2009/0076516 A1* | 3/2009 | Lowry et al. | 606/90 |
| 2009/0287062 A1* | 11/2009 | Farley | 600/231 |
| 2010/0057134 A1* | 3/2010 | Lowry et al. | 606/286 |
| 2014/0031874 A1* | 1/2014 | Kucharzyk et al. | 606/279 |

* cited by examiner

ANTERIOR CERVICAL RETRACTOR SYSTEM

CROSS-REFERENCES TO RELATED APPLICATIONS

This application claims priority from U.S. Patent Application No. 61/474,805 filed Apr. 13, 2011.

STATEMENT REGARDING FEDERALLY SPONSORED RESEARCH

Not Applicable.

BACKGROUND OF THE INVENTION

1. Field of the Invention

The invention relates to a system for orthopedic or neurological surgery on a patient, and more particularly to a retractor system for anterior cervical spine surgery.

2. Description of the Related Art

Anterior cervical fusion is one of the most commonly performed spine procedures in the world. One of the nuances in anterior cervical spine surgery is adequate retraction. There have been no recent advances in anterior cervical retraction.

One commonly used anterior cervical retractor system is part of the TrimLine® anterior cervical discectomy & fusion instrument set available from Medtronic Sofamor Danek. Another commonly used anterior cervical retractor system is the Shadow-Line® anterior cervical fusion retractor and distraction system available from Cardinal Health V. Mueller® Neuro/Spine Products. The TrimLine® and Shadow-Line® anterior cervical retractor systems do provide ease of use, multiple blade lengths, and a good self-retaining mechanism. However, the TrimLine® and Shadow-Line® anterior cervical retractor systems can still have shortcomings including displacement of the retractor, tissue creep into the operative field, and the need to reposition the retractors in multilevel cases. In particular, one of the difficulties with the TrimLine® and Shadow-Line® anterior cervical retractor systems is that there is more resistance on the blade retracting the trachea and esophagus medially as compared to the blade retracting the carotid artery laterally. This results in the retractor wanting to become displaced out of the wound when retracting on the blades.

Another of the nuances in anterior cervical spine surgery is placement of the anterior cervical plate. Traditional methods of plate placement involve the surgeon holding the plate with a device in one hand and then fixating the plate with a screw driver in the other hand. This can result in the plate sliding or becoming angled as the surgeon switches instruments with his/her hand during screw placement. Plate placement can be particularly important with extendable plate systems.

For example, Globus Medical sells a plate called the XTEND® anterior cervical plate that is a system that not only addresses a patients' immediate needs but also considers long-term treatment. The XTEND® anterior cervical plate provides surgeons with the ability to later treat adjacent levels as needed. An extender plate may be added to any primary plate with no disruption to the primary construct. The XTEND® primary plate preserves intact adjacent levels and accepts an extender plate if adjacent levels need stabilization. When treating an adjacent level with an extender plate, the primary plate and screws remain in place, preserving primary bone purchase and an extender plate can be placed adjacent to any primary plate without disrupting the primary plate or screws, eliminating the need to remove the primary construct. Plate placement is particularly important with the primary plate as a primary plate placed crooked can impede the ability to place an extender plate onto the primary plate in the future.

What is needed therefore is an anterior cervical retractor system that would address these shortcomings and would make it significantly easier for a surgeon to apply the anterior cervical plate to the vertebra.

SUMMARY OF THE INVENTION

The present invention addresses the foregoing needs by providing a system for orthopedic or neurological surgery on a patient positioned on an operating table. In one non-limiting application of the system, the surgery is anterior cervical spine surgery. The system includes a retractor support arm; a table mounting assembly for securing the retractor support arm to the operating table; a first blade mounting arm slidably engaging the retractor support arm; a second blade mounting arm slidably engaging the retractor support arm in spaced relationship with respect to the first blade mounting arm; a first retractor blade connected to the first blade mounting arm; and a second retractor blade connected to the second blade mounting arm. The first blade mounting arm and the second blade mounting arm can be moved away from each other and secured on the retractor support arm such that the first retractor blade and the second retractor blade hold back soft tissues of the patient on opposite sides of a surgical incision in the patient.

In the system of the invention, the table mounting assembly can include a clamp for securing the retractor support arm to the operating table. The clamp can be structured to secure the retractor support arm to a side rail of the operating table. The first retractor blade can have a width of 30 millimeters to 105 millimeters and a longitudinal length of 30 millimeters to 75 millimeters, and the second retractor blade can have a width of 30 millimeters to 105 millimeters and a longitudinal length of 30 millimeters to 75 millimeters.

The first retractor blade can have a first section connected to the first blade mounting arm and a second section that extends laterally from the first section of the first retractor blade. The second retractor blade can have a first section connected to the second blade mounting arm and a second section that extends laterally from the first section of the second retractor blade. The second section of the first retractor blade can extend laterally from the first section of the first retractor blade at an angle of 45 to 60 degrees with respect to a top edge of the first section of the first retractor blade. The second section of the second retractor blade can extend laterally from the first section of the second retractor blade at an angle of 45 to 60 degrees with respect to a top edge of the first section of the second retractor blade.

The system can include a first fastener for securing the first blade mounting arm on the retractor support arm to prevent sliding movement of the first blade mounting arm on the retractor support arm; and a second fastener for securing the second blade mounting arm on the retractor support arm to prevent sliding movement of the second blade mounting arm on the retractor support arm.

In another aspect, the invention provides a system for orthopedic surgery on a patient positioned on an operating table. The system includes a retractor support arm; a table mounting assembly for securing the retractor support arm to the operating table; a first blade mounting arm slidably engaging the retractor support arm; a second blade mounting arm slidably engaging the retractor support arm in spaced relationship with respect to the first blade mounting arm; a first retractor blade connected to the first blade mounting arm; a second retractor blade connected to the second blade mounting arm; and a plate support assembly for releasably engaging an orthopedic plate. The plate support assembly slidably engages at least one of the retractor support arm or the first blade mounting arm or the second blade mounting arm. The first blade mounting arm and the second blade mounting arm can be moved away from each other and secured on the retractor support arm such that the first retractor blade and the second retractor blade hold back soft tissues of the patient on opposite sides of a surgical incision in the patient.

The system can include a drill guide, and a drill guide support assembly for releasably engaging the drill guide. The drill guide support assembly slidably engages at least one of the retractor support arm or the first blade mounting arm or the second blade mounting arm. In one version of the system, the plate support assembly slidably engages the first blade mounting arm.

The system can include a fastener for securing the plate support assembly to first blade mounting arm to prevent sliding movement of the plate support assembly on the first blade mounting arm. In the system, the orthopedic plate can include a mounting hole, and the plate support assembly can include a shaft, and the shaft releasably engages the mounting hole of the orthopedic plate.

The table mounting assembly can include a clamp for securing the retractor support arm to the operating table. In one form, the clamp is structured to secure the retractor support arm to a side rail of the operating table.

In the system, the first retractor blade can have a width of 30 millimeters to 105 millimeters and a longitudinal length of 30 millimeters to 75 millimeters, and the second retractor blade can have a width of 30 millimeters to 105 millimeters and a longitudinal length of 30 millimeters to 75 millimeters. In one form, the first retractor blade has a first section connected to the first blade mounting arm and has a second section that extends laterally from the first section of the first retractor blade, and the second retractor blade has a first section connected to the second blade mounting arm and has a second section that extends laterally from the first section of the second retractor blade.

The second section of the first retractor blade can extend laterally from the first section of the first retractor blade at an angle of 45 to 60 degrees with respect to a top edge of the first section of the first retractor blade, and the second section of the second retractor blade can extend laterally from the first section of the second retractor blade at an angle of 45 to 60 degrees with respect to a top edge of the first section of the second retractor blade.

In the system for orthopedic surgery, the surgery can be spine surgery and the orthopedic plate can be a spine plate. The surgery can be anterior cervical spine surgery and the orthopedic plate can be an anterior cervical plate.

In yet another aspect, the invention provides a method for surgery on a patient positioned on an operating table. The method can include the steps of making an incision in the patient; securing a retractor support arm to the operating table; positioning a first blade mounting arm on the retractor support arm such that a first retractor blade of the first blade mounting arm is positioned in the incision; positioning a second blade mounting arm on the retractor support arm such that a second retractor blade of the second blade mounting arm is positioned in the incision; moving the first blade mounting arm and the second blade mounting arm away from each other such that the first retractor blade and the second retractor blade hold back soft tissues of the patient on opposite sides of the incision in the patient; and securing the first blade mounting arm and the second blade mounting arm on the retractor support arm.

The method can further include the steps of providing an orthopedic plate; releasably securing a distal end of a plate support assembly to the plate; and releasably securing a proximal end of the plate support assembly to at least one of the retractor support arm or the first blade mounting arm or the second blade mounting arm.

In the method for orthopedic surgery, the surgery can be spine surgery and the orthopedic plate can be a spine plate. The surgery can be anterior cervical spine surgery and the orthopedic plate can be an anterior cervical plate.

It is an advantage of the invention to provide an anterior cervical retractor system that eliminates or minimizes displacement of the retractor.

It is another advantage of the invention to provide an anterior cervical retractor system that eliminates or minimizes tissue creep into the operative field.

It is yet another advantage of the invention to provide an anterior cervical retractor system that eliminates or minimizes the need to reposition the retractors in multilevel cases.

It is still another advantage of the invention to provide an anterior cervical retractor system that makes it easier for a surgeon to apply an anterior cervical plate.

It is yet another advantage of the invention to provide an anterior cervical retractor system that helps the surgeon hold the anterior cervical plate in position during application of the plate.

It is still another advantage of the invention to provide an anterior cervical retractor system that allows a primary plate to be placed away from the adjacent disc spaces to allow for screw placement in the vertebral body if an extension plate is added in the future.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
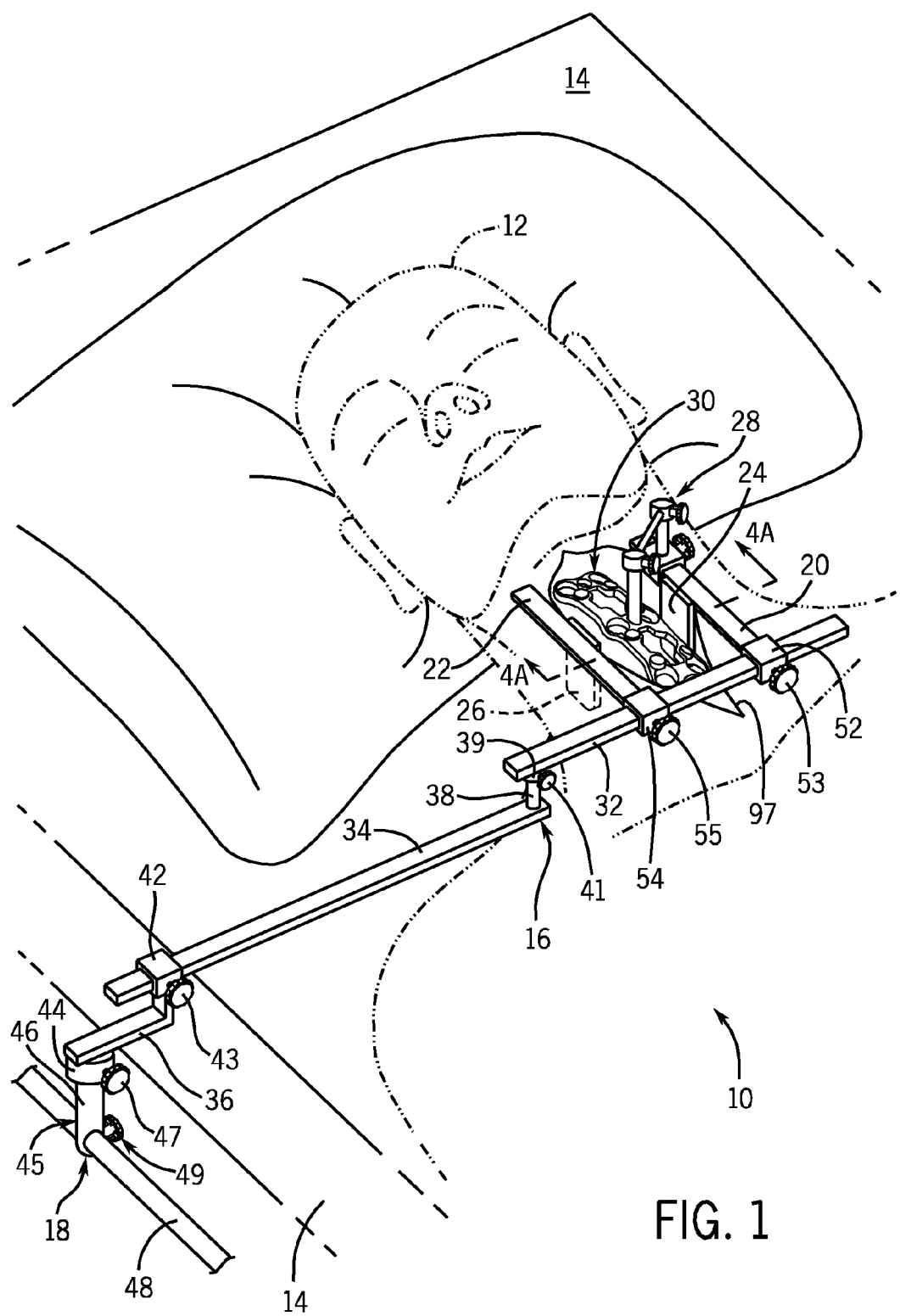
FIG. 1 is a top front perspective view of one version of an anterior cervical retractor system according to the invention.
Figure 2:
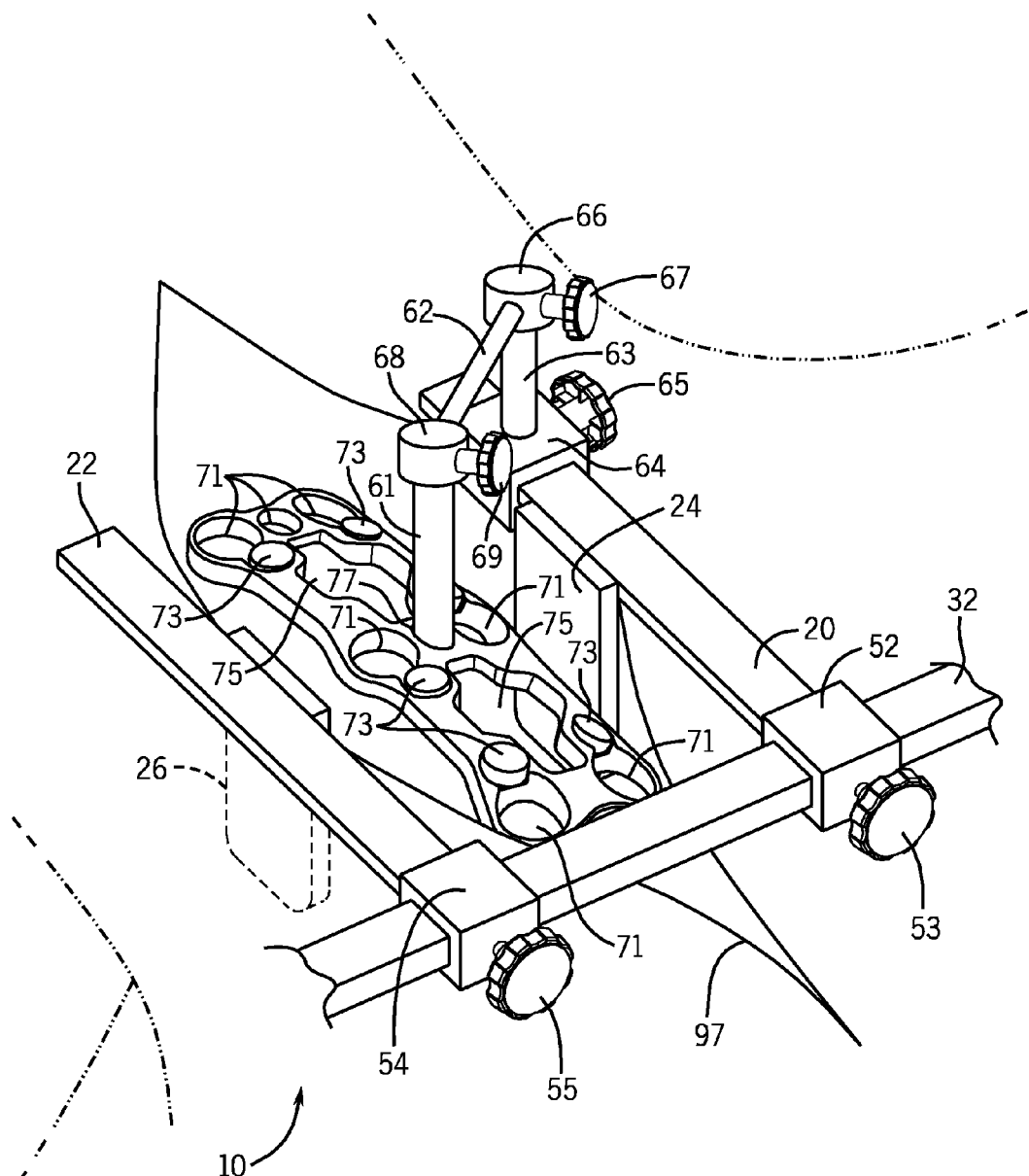
FIG. 2 is a top front detailed perspective view of the anterior cervical retractor system of FIG. 1.
Figure 3:
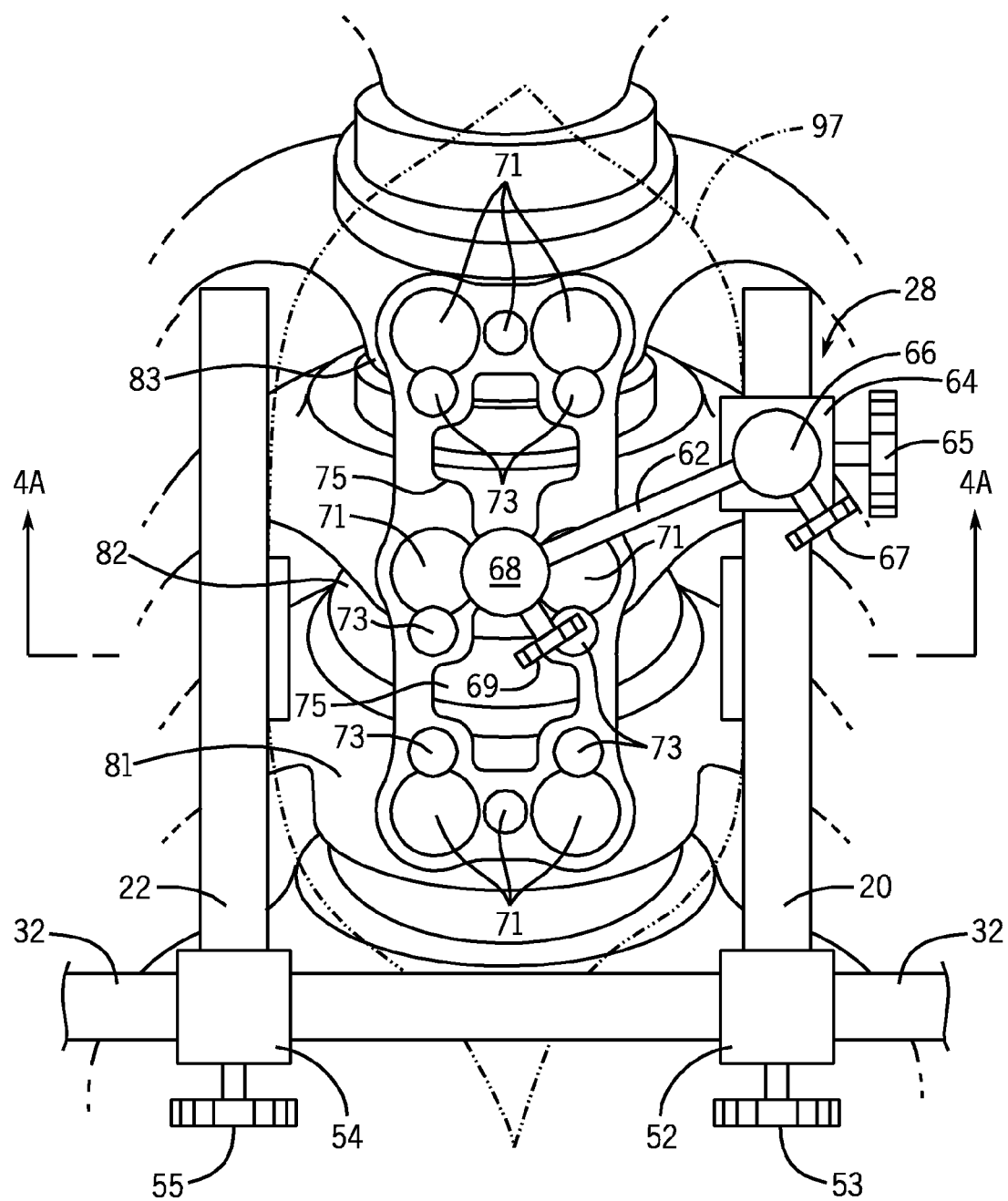
FIG. 3 is a top view of the anterior cervical retractor system of FIG. 1.

If surgery is needed to alleviate nerve or spinal cord compression in a patient, a surgeon may perform a procedure called an anterior cervical discectomy and fusion. In this procedure, the surgeon makes an incision in the front of the neck to reach the cervical spine. Tissues are retracted to reveal the proper level in the cervical spine. The disc is removed and the space is filled with bone graft or an implant. A cervical plate can be screwed into the top and bottom vertebral bodies which stabilizes the cervical spine facilitating fusion and healing.

Referring to FIGS. 1 to 5, there is shown one version of an anterior cervical retractor system 10 according to the invention. The anterior cervical retractor system 10 can be used in an anterior cervical discectomy and fusion. While the invention is shown and described with reference to an anterior cervical discectomy, the system can be used for other orthopedic procedures that use a retractor system and/or an orthopedic plate.

For a surgery using the anterior cervical retractor system 10, a patient 12 is positioned on an operating table 14. The system 10 includes a retractor support arm 16, a table mounting assembly 18 for securing the retractor support arm 16 to the operating table 14, a first blade mounting arm 20 that slidably engages the retractor support arm 16, a second blade mounting arm 22 that slidably engages the retractor support arm 16 in spaced relationship with respect to the first blade mounting arm 20, a first retractor blade 24 connected to the first blade mounting arm 20, a second retractor blade 26 connected to the second blade mounting arm 22, and a plate support assembly 28 for releasably engaging an orthopedic plate 30. In the version of the system 10 shown, the plate support assembly 28 slidably engages the first blade mounting arm 20. Alternatively, the plate support assembly 28 could slidably engage the retractor support arm 16 or the second blade mounting arm 22.

The retractor support arm 16 includes a first rectangular bar 32, a second rectangular bar 34 and a third rectangular bar 36. A pin 38 extends upward from the second rectangular bar 34 and is received in a downwardly opening sleeve 39 in the first rectangular bar 32. A set screw 41 secures the pin 38 in the sleeve 39 after the desired rotational position of the first rectangular bar 32 and the second rectangular bar 34 is achieved. The second rectangular bar 34 can slidingly translate in a rectangular collar 42 that is attached to the third rectangular bar 36. A set screw 43 secures the second rectangular bar 34 in the collar 42 after the desired position of the third rectangular bar 36 and the second rectangular bar 34 is achieved.

The table mounting assembly 18 includes a downwardly opening sleeve 44 that is attached to the third rectangular bar 36. A clamp 45 has a shaft 46 that is secured in the sleeve 44 by a set screw 47 after the desired rotational position of the third rectangular bar 36 and the clamp 45 is achieved. The clamp 45 is secured to a side rail 48 of the operating table 14 by a set screw 49.

The first blade mounting arm 20 is connected to a rectangular collar 52 that can slidingly translate over the first rectangular bar 32 of the retractor support arm 16. A set screw 53 secures the first rectangular bar 32 in the collar 52 after the desired position of the first rectangular bar 32 and the first blade mounting arm 20 is achieved. In the version of the system shown, the first retractor blade 24 is integral with the first blade mounting arm 20. However, the first retractor blade 24 can be removably connected to the first blade mounting arm 20 by a fastener such as a clamp.

The second blade mounting arm 22 is connected to a rectangular collar 54 that can slidingly translate over the first rectangular bar 32 of the retractor support arm 16. A set screw 55 secures the first rectangular bar 32 in the collar 54 after the desired position of the first rectangular bar 32 and the second blade mounting arm 22 is achieved. In the version of the system shown, the second retractor blade 26 is integral with the second blade mounting arm 22. However, the second retractor blade 26 can be removably connected to the second blade mounting arm 22 by a fastener such as a clamp.

In one form, each of the first retractor blade 24 and the second retractor blade 26 has a width of 30 millimeters to 105 millimeters. In one form, each of the first retractor blade 24 and the second retractor blade 26 has a width of 30 millimeters or greater, or 35 millimeters or greater, or 40 millimeters or greater, or 45 millimeters or greater, or 50 millimeters or greater, or 55 millimeters or greater, or 60 millimeters or greater, or 65 millimeters or greater, or 70 millimeters or greater, or 75 millimeters or greater, or 80 millimeters or greater, or 85 millimeters or greater, or 90 millimeters or greater, or 95 millimeters or greater, or 100 millimeters or greater. In one form, each of the first retractor blade 24 and the second retractor blade 26 has a longitudinal length of 30 millimeters to 75 millimeters. In one form, each of the first retractor blade 24 and the second retractor blade 26 has a longitudinal length of 30 millimeters or greater, or 35 millimeters or greater, or 40 millimeters or greater, or 45 millimeters or greater, or 50 millimeters or greater, or 55 millimeters or greater, or 60 millimeters or greater, or 65 millimeters or greater, or 70 millimeters or greater, or 75 millimeters or greater. Preferably, each of the first retractor blade 24 and the second retractor blade 26 comprises a radiolucent material.

Figure 4A:
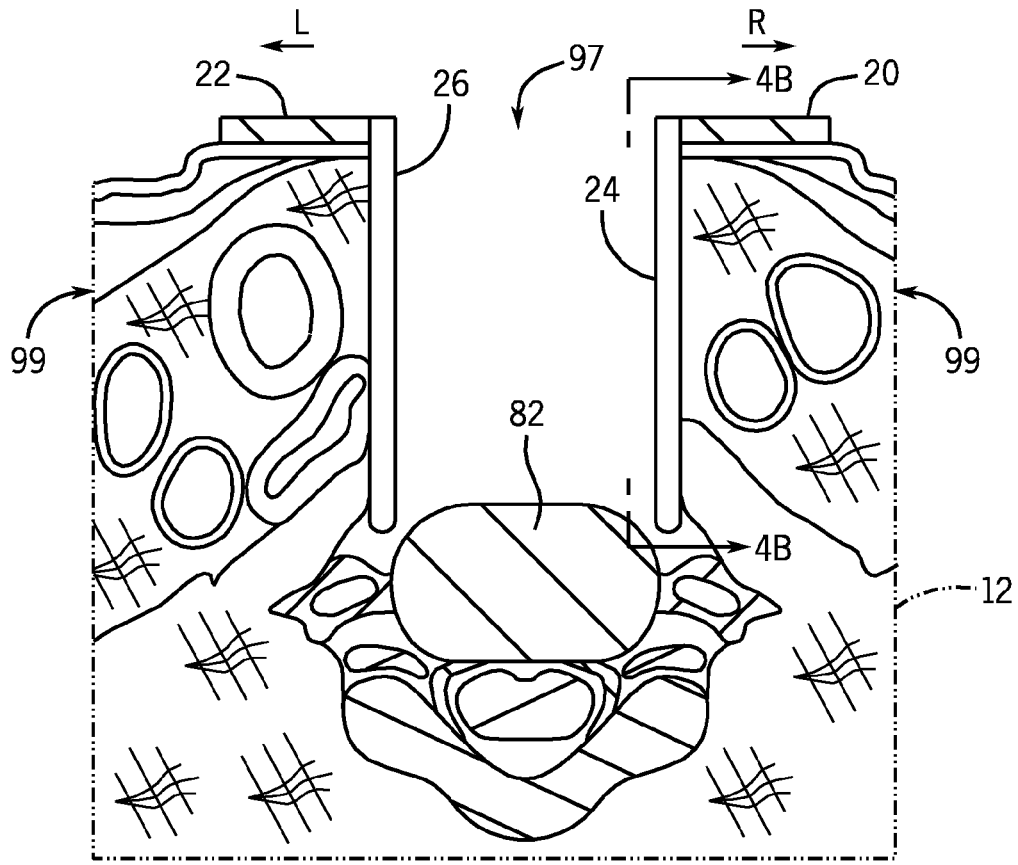
FIG. 4A is a cross-sectional view taken along line 4A-4A of FIG. 1 with the orthopedic plate and the plate support assembly removed.
Figure 4B:
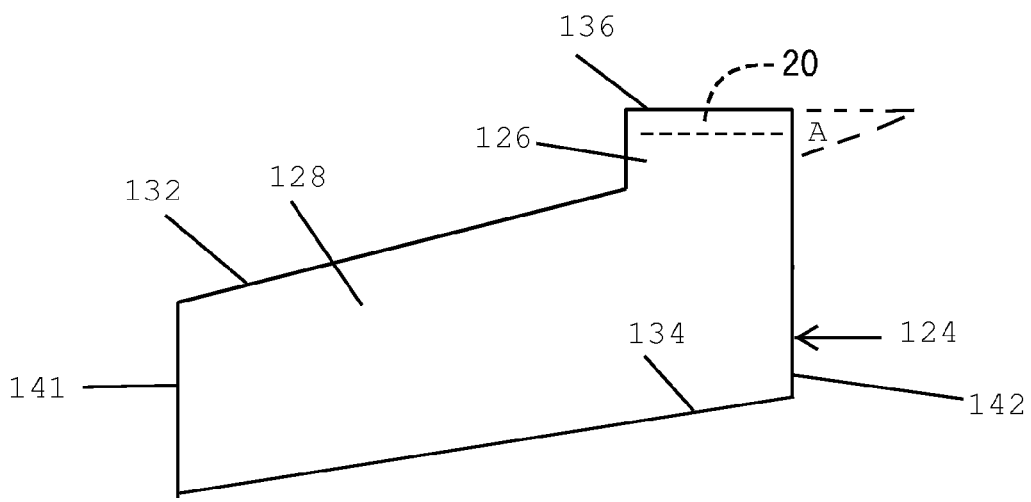
FIG. 4B is a view taken along line 4B-4B of FIG. 4A showing another embodiment of a retractor blade for use with the anterior cervical retractor system according to the invention.

Looking at FIG. 4B, another embodiment of a retractor blade 124 for use with the anterior cervical retractor system 10. In some cases, such as C2 fracture, a screw must be placed across this fracture in an inferior to superior trajectory. However, to get this trajectory, the incision is made over the C5-6 area and the surgeon has to dissect and look superiorly to get to the base of C2 and then place the screw. Angled blades are advantageous for this surgical procedure.

In FIG. 4B, the retractor blade 124 has a first section 126 connected to the first blade mounting arm 20 and has a second section 128 that extends laterally from the first section 126 of the retractor blade 124. The first section 126 has a top edge 136. The second section 128 has an upper edge 132 and a lower edge 134. The upper edge 132 and/or the lower edge 134 of the second section 128 may form an angle A with respect to the top edge 136 of the first section 126. The angle A may be 10 to 80 degrees, preferably 20 to 70 degrees, and more preferably 45 to 60 degrees. The distance from the top edge 136 to the lower edge 134 can be 25 to 100 millimeters, and preferably 50 to 75 millimeters. The distance from the side edge 141 to the side edge 142 can be 25 to 200 millimeters, and preferably 50 to 75 millimeters.

In the version of the anterior cervical retractor system 10 shown, the plate support assembly 28 includes a first mounting shaft 61, a second mounting shaft 62, and a third mounting shaft 63. Optionally, the first mounting shaft 61, the second mounting shaft 62, and the third mounting shaft 63 can be fabricated from deformable flexible materials that maintain shape after deformation. The third mounting shaft 63 is connected to a rectangular collar 64 that can slidingly translate over the first blade mounting arm 20. A set screw 65 secures the first blade mounting arm 20 in the collar 64 after the desired position of the third mounting shaft 63 and the first blade mounting arm 20 is achieved. An end cap 66 is placed over the third mounting shaft 63. The end cap 66 is connected to the second mounting shaft 62, and a set screw 67 secures the third mounting shaft 63 in the end cap 66 after the desired rotational position of the third mounting shaft 63 and the second mounting shaft 62 is achieved. An end cap 68 is placed over the first mounting shaft 61. The end cap 68 is connected to the second mounting shaft 62, and a set screw 69 secures the first mounting shaft 61 in the end cap 68 after the desired rotational position of the first mounting shaft 61 and the second mounting shaft 62 is achieved.

The anterior cervical plate 30 includes a plurality of screw holes 71 and bone screws 73. Two visualization windows 75 extend through the plate 30. The plate 30 includes a central mounting hole 77.

The first mounting shaft 61 releasably engages the plate 30. In one non-limiting example embodiment, the central mounting hole 77 in the plate 30 includes internal threads and the outer surface of the distal end of the first mounting shaft 61 includes external threads such that the first mounting shaft 61 can be threaded into the central mounting hole 77 in the plate 30 to removably fasten the first mounting shaft 61 to the plate 30. After the plate 30 is secured to the vertebral bodies 81, 82, 83, the first mounting shaft 61 can be unthreaded from the central mounting hole 77 in the plate 30. In another non-limiting example embodiment, bayonet attachment, in which an outwardly extending pin on the distal end of the first mounting shaft 61 is inserted and turned into an L-shaped groove in the central mounting hole 77 in the plate 30, can be used to removably fasten the first mounting shaft 61 to the plate 30. After the plate 30 is secured to the vertebral bodies, the first mounting shaft 61 can be removed from the central mounting hole 77 in the plate 30. In yet another non-limiting example embodiment, the first mounting shaft 61 can be hollow and a spring button can be mounted in the hollow distal end of the first mounting shaft 61. The button of the spring button passes through an aperture in the wall of the first mounting shaft 61, and the movable button can be used to engage a groove in the central mounting hole 77 in the plate 30 to removably fasten the first mounting shaft 61 to the plate 30. After the plate 30 is secured to the vertebral bodies, the first mounting shaft 61 can be disengaged from the central mounting hole 77 in the plate 30. The first mounting shaft 61 can be rotated and/or moved up or down in the end cap 68 to place the plate 30 in the proper position on the top and bottom vertebral bodies. The set screw 69 is then tightened on the first mounting shaft 61 in the end cap 68 to keep the plate 30 in the proper position on the top and bottom vertebral bodies. Optionally, the end cap 68 can be replaced with a hollow circular collar (similar to rectangular collar 52) that provides for even more upward movement of the first mounting shaft 61 and allows for the use of an extended length first mounting shaft 61.

Figure 5:
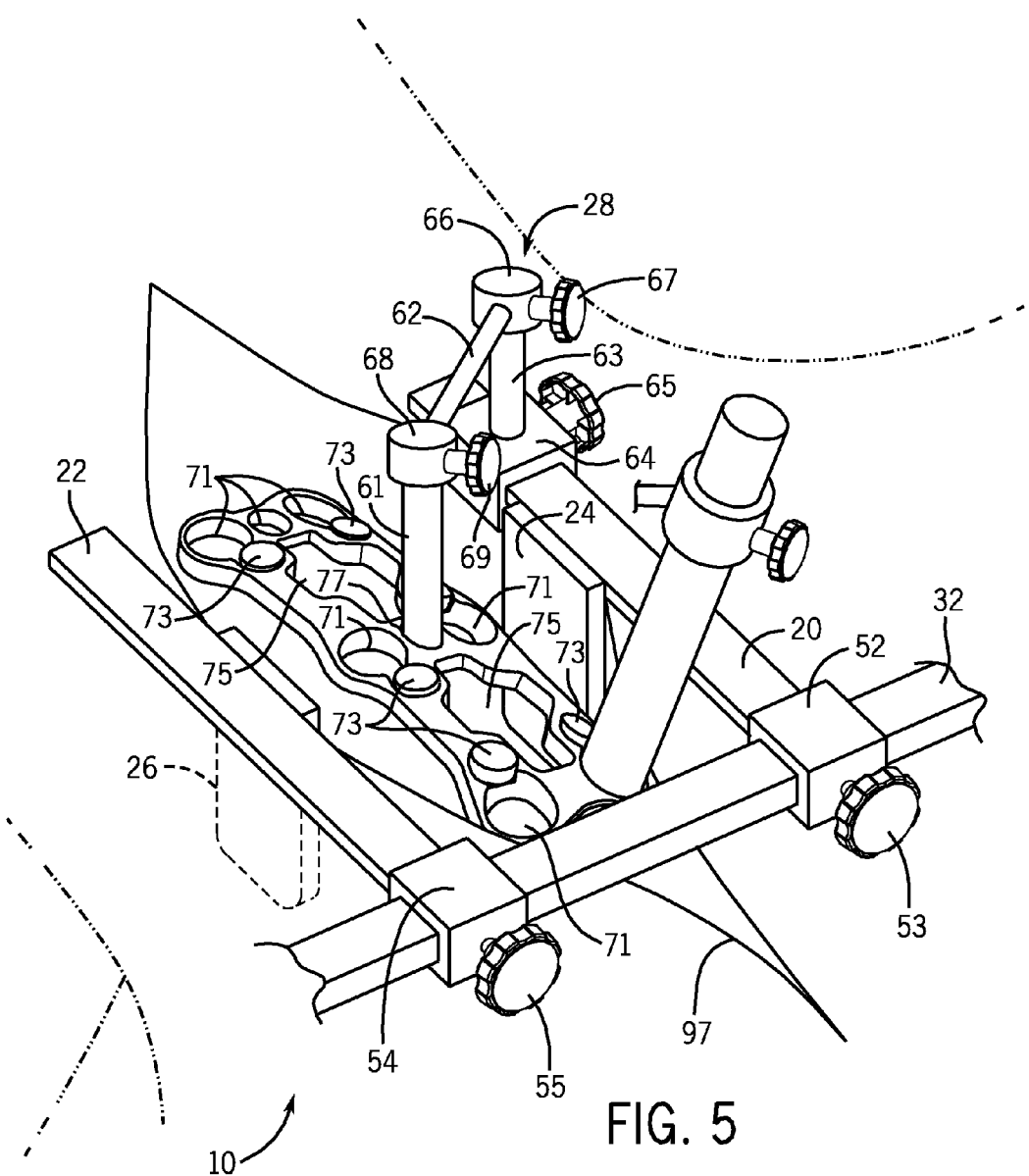
FIG. 5 is a top front detailed perspective view similar to FIG. 2 showing a drill guide fastened to the cervical plate.

Looking at FIG. 5, the anterior cervical retractor system 10 can also include a tubular drill guide 91 with a drill guide support assembly 92 for releasably engaging the drill guide 91. The drill guide support assembly 92 can slidably engage the first blade mounting arm 20, the retractor support arm 16 or the second blade mounting arm 22. The drill guide support assembly 92 includes a hollow circular collar 93, a shaft 94 connected to the collar 93, and a set screw 95. The set screw 95 secures the drill guide 91 in the collar 93 after the desired position of the drill guide 91 in a hole of the plate 30 is achieved. The shaft 94 can be connected to the first blade mounting arm 20 using a rectangular collar (such as rectangular collar 64) that can slidingly translate over the first blade mounting arm 20 and a set screw (such as set screw 65).

After an incision 97 is made in the patient, components of the anterior cervical retractor system 10 are assembled as shown in FIG. 1-5. The first retractor blade 24 and the second retractor blade 26 are positioned in the incision 97 as shown in FIG. 4. The first blade mounting arm 20 (and attached first retractor blade 24) are moved in direction R and the second blade mounting arm 22 (and attached second retractor blade 26) are moved in direction L to retract soft tissues 99 of the patient 12. The set screw 53 is tightened to secure the first rectangular bar 32 in the collar 52 after the desired position of the first rectangular bar 32 and the first blade mounting arm 20 is achieved. The set screw 55 is tightened to secure the first rectangular bar 32 in the collar 54 after the desired position of the first rectangular bar 32 and the second blade mounting arm 22 is achieved. The first retractor blade 24 and the second retractor blade 26 hold back soft tissues 99 of the patient 12 on opposite sides of the surgical incision 97 in the patient 12. The plate 30 can be placed on the vertebral bodies 81, 82, 83, and the plate support assembly 28 can be used to hold the plate 30 in place on the vertebral bodies 81, 82, 83 as described above. Likewise, the drill guide 91 can be held in place on the plate 30 as described above.

The invention provides an anterior cervical retractor system that eliminates or minimizes displacement of the retractor. The table mounting assembly 18 helps hold the retractor in place and provides better exposure. The table mounting assembly 18 stabilizes the retractor. The table mounting assembly 18 also allows for wider retractor blades (e.g., 30 millimeters or greater) to be used to retract more tissue for multilevel cases (i.e., a discectomy on more than one level of the spine) as the retractor system is stabilized to the operating table.

The invention also provides an anterior cervical retractor system that eliminates or minimizes tissue creep into the operative field, for example, by the use of wider retractor blades.

The invention also provides an anterior cervical retractor system that eliminates or minimizes the need to reposition the retractors in multilevel cases. Because the retractor system is table-mounted, wider blades can be used to hold back more tissue without displacement of the retractor out of the wound. This negates having to replace the retractor multiple times during multilevel anterior cervical fusion cases.

The invention also provides an anterior cervical retractor system that makes it easier for a surgeon to apply an anterior cervical plate. The plate support assembly 28 keeps the plate 30 in place on the vertebral bodies 81, 82, 83 without the surgeon having to hold the plate 30. Likewise, the drill guide support assembly 92 keeps the drill guide 91 positioned on the plate 30 without the surgeon having to hold the drill guide 91. Thus, the retractor system helps the surgeon hold the anterior cervical plate in position during application of the plate. Traditional methods of plate placement involve the surgeon holding the plate with a device in one hand and then fixating the plate with a screw driver in the other hand. This can result in the plate sliding or becoming angled as the surgeon switches instruments with his/her hand during screw placement.

Plate placement is particularly important with extendable plates as a plate placed crooked can impede the ability to extend onto this plate in the future. Also, the plate needs to be placed away from the adjacent disc spaces to allow for screw placement in the vertebral body if an extension plate is added in the future. Adequate plate placement can be facilitated as the plate is able to be held in place by a system according the invention independent of the surgeon. This allows for the plate position to be adjusted and held into place. The flexible shaft attaches to the middle of the plate and also attach to the fixed retractor system to allow the plate to be held in this optimal position during fixation. The surgeon could choose to check position with fluoroscopy or just direct visualization prior to screw placement. The surgeon would then be able to place screws into the plate using both hands while the plate is being held in place by the plate support assembly. A screw could be placed at the superior and inferior end of the plate to further lock it into position and the plate support assembly can be removed for placement of the remaining screws.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A retractor system for surgery on a patient positioned on an operating table, the system comprising:
   a retractor support arm;
   a table mounting assembly for securing the retractor support arm to the operating table;
   a first blade mounting arm slidably engaging the retractor support arm, the first blade mounting arm defining a longitudinal axis of the first blade mounting arm;
   a second blade mounting arm slidably engaging the retractor support arm in spaced relationship with respect to the first blade mounting arm, the second blade mounting arm defining a longitudinal axis of the second blade mounting arm;
   a first retractor blade integrally connected to the first blade mounting arm such that the first retractor blade is not removably connected to the first blade mounting arm and such that the first retractor blade is non-rotatably fixed orthogonal to the longitudinal axis of the first blade mounting arm; and
   a second retractor blade connected to the second blade mounting arm such that the second retractor blade is non-rotatably fixed orthogonal to the longitudinal axis of the second blade mounting arm,
   wherein the first blade mounting arm and the second blade mounting arm can be moved away from each other and secured on the retractor support arm such that the first retractor blade and the second retractor blade hold back soft tissues of the patient on opposite sides of a surgical incision in the patient.

2. The system of claim 1 wherein:
   the table mounting assembly includes a clamp for securing the retractor support arm to the operating table.

3. The system of claim 2 wherein:
   the clamp is structured to secure the retractor support arm to a side rail of the operating table.

4. The system of claim 1 wherein:
   the first retractor blade has a width of 30 millimeters to 105 millimeters and a longitudinal length of 30 millimeters to 75 millimeters, and
   the second retractor blade has a width of 30 millimeters to 105 millimeters and a longitudinal length of 30 millimeters to 75 millimeters.

5. The system of claim 1 wherein:
   the first retractor blade has a first section connected to the first blade mounting arm and has a second section that extends laterally from the first section of the first retractor blade, and
   the second retractor blade has a first section connected to the second blade mounting arm and has a second section that extends laterally from the first section of the second retractor blade.

6. The system of claim 5 wherein:
   the second section of the first retractor blade extends laterally from the first section of the first retractor blade at an angle of 45 to 60 degrees with respect to a top edge of the first section of the first retractor blade, and
   the second section of the second retractor blade extends laterally from the first section of the second retractor blade at an angle of 45 to 60 degrees with respect to a top edge of the first section of the second retractor blade.

7. The system of claim 1 further comprising:
   a first fastener for securing the first blade mounting arm on the retractor support arm to prevent sliding movement of the first blade mounting arm on the retractor support arm; and
   a second fastener for securing the second blade mounting arm on the retractor support arm to prevent sliding movement of the second blade mounting arm on the retractor support arm.

8. A system for orthopedic surgery on a patient positioned on an operating table, the system comprising:
   a retractor support arm;
   a table mounting assembly for securing the retractor support arm to the operating table;
   a first blade mounting arm slidably engaging the retractor support arm;
   a second blade mounting arm slidably engaging the retractor support arm in spaced relationship with respect to the first blade mounting arm;
   a first retractor blade integrally connected to the first blade mounting arm such that the first retractor blade is not removably connected to the first blade mounting arm and such that the first retractor blade is non-rotatably fixed to the first blade mounting arm;
   a second retractor blade connected to the second blade mounting arm such that the second retractor blade is non-rotatably fixed to the second blade mounting arm; and
   a plate support assembly for releasably engaging an orthopedic plate, the plate support assembly slidably engaging at least one of the retractor support arm or the first blade mounting arm or the second blade mounting arm,
   wherein the first blade mounting arm and the second blade mounting arm can be moved away from each other and secured on the retractor support arm such that the first retractor blade and the second retractor blade hold back soft tissues of the patient on opposite sides of a surgical incision in the patient.

9. The system of claim 8 further comprising:
   a drill guide; and
   a drill guide support assembly for releasably engaging the drill guide, the drill guide support assembly slidably engaging at least one of the retractor support arm or the first blade mounting arm or the second blade mounting arm.

10. The system of claim 8 wherein:
    the plate support assembly slidably engages the first blade mounting arm.

11. The system of claim 10 further comprising:
a fastener for securing the plate support assembly to first blade mounting arm to prevent sliding movement of the plate support assembly on the first blade mounting arm.

12. The system of claim 10 wherein:
the orthopedic plate includes a mounting hole, and
the plate support assembly includes a shaft, and
the shaft releasably engages the mounting hole of the orthopedic plate.

13. The system of claim 8 wherein:
the table mounting assembly includes a clamp for securing the retractor support arm to the operating table.

14. The system of claim 13 wherein:
the clamp is structured to secure the retractor support arm to a side rail of the operating table.

15. The system of claim 8 wherein:
the first retractor blade has a width of 30 millimeters to 105 millimeters and a longitudinal length of 30 millimeters to 75 millimeters, and
the second retractor blade has a width of 30 millimeters to 105 millimeters and a longitudinal length of 30 millimeters to 75 millimeters.

16. The system of claim 8 wherein:
the first retractor blade has a first section connected to the first blade mounting arm and has a second section that extends laterally from the first section of the first retractor blade, and
the second retractor blade has a first section connected to the second blade mounting arm and has a second section that extends laterally from the first section of the second retractor blade.

17. The system of claim 16 wherein:
the second section of the first retractor blade extends laterally from the first section of the first retractor blade at an angle of 45 to 60 degrees with respect to a top edge of the first section of the first retractor blade, and
the second section of the second retractor blade extends laterally from the first section of the second retractor blade at an angle of 45 to 60 degrees with respect to a top edge of the first section of the second retractor blade.

18. The system of claim 8 wherein:
the surgery is anterior cervical spine surgery and the orthopedic plate is an anterior cervical plate.

* * * * *